(12) United States Patent
Harada et al.

(10) Patent No.: US 7,923,687 B2
(45) Date of Patent: Apr. 12, 2011

(54) RADIATION IMAGE CAPTURING SYSTEM, CONTROLLER, PROGRAM, AND RADIATION IMAGE CAPTURING METHOD

(75) Inventors: Daiki Harada, Minami-ashigara (JP); Yasunori Ohta, Yokohama (JP); Naoyuki Nishino, Minami-ashigara (JP); Naoki Mochizuki, Minami-ashigara (JP); Wataru Ito, Hadano (JP); Yoshiro Kitamura, Yokohama (JP); Eiichi Kito, Minami-ashigara (JP); Akio Sato, Kawasaki (JP)

(73) Assignee: FUJIFILM Corporation, Tokyo (JP)

( * ) Notice: Subject to any disclaimer, the term of this patent is extended or adjusted under 35 U.S.C. 154(b) by 56 days.

(21) Appl. No.: 12/412,059

(22) Filed: Mar. 26, 2009

(65) Prior Publication Data

US 2009/0242767 A1  Oct. 1, 2009

(30) Foreign Application Priority Data

Mar. 27, 2008 (JP) .................. 2008-083934
Feb. 16, 2009 (JP) .................. 2009-032200

(51) Int. Cl.
*G01J 1/00* (2006.01)
(52) U.S. Cl. ................................. 250/336.1
(58) Field of Classification Search .... 250/336.1–336.2; 378/80, 87, 96, 62, 95, 207
See application file for complete search history.

(56) References Cited

U.S. PATENT DOCUMENTS

2006/0120512 A1   6/2006   Watanabe
2008/0049996 A1*  2/2008   Marshall et al. .............. 382/128

FOREIGN PATENT DOCUMENTS

| EP | 1 413 921 A1 | 4/2004 |
| EP | 1 530 162 A2 | 5/2005 |
| JP | 03-115960 | 5/1991 |
| JP | 3494683 B2 | 6/1995 |
| JP | 2000-105297 A | 4/2000 |
| JP | 2000-166908 A | 6/2000 |
| JP | 2004-298217 A | 10/2004 |

OTHER PUBLICATIONS

EP Communication, dated Jul. 17, 2009, issued in corresponding EP Application No. 09003687.2, 8 pages.

* cited by examiner

*Primary Examiner* — David P Porta
*Assistant Examiner* — Kiho Kim
(74) *Attorney, Agent, or Firm* — Sughrue Mion, PLLC

(57) ABSTRACT

A radiation image capturing system includes an image capturing apparatus for acquiring radiation image information of a subject by controlling a radiation source according to predetermined image capturing conditions, an image capturing order supply apparatus for supplying an image capturing order including the image capturing conditions, and a controller for controlling the image capturing apparatus according to the image capturing order. The controller includes an image capturing order changer for changing the image capturing order, an image capturing detail editor for editing image capturing details of the radiation image information acquired when the image capturing apparatus is controlled according to the image capturing order, and an image capturing detail supply unit for supplying the edited image capturing details.

9 Claims, 6 Drawing Sheets

RADIATION IMAGE CAPTURING SYSTEM, CONTROLLER, PROGRAM, AND RADIATION IMAGE CAPTURING METHOD

BACKGROUND OF THE INVENTION

1. Field of the Invention

The present invention relates to a radiation image capturing system and a radiation image capturing method for capturing radiation image information of a subject with an image capturing apparatus, a controller for controlling an image capturing apparatus according to an image capturing order including image capturing conditions, and a program executed in a controller for controlling an image capturing apparatus according to an image capturing order.

2. Description of the Related Art

Certain medical organizations, such as hospitals and the like, incorporate a radiation image capturing system combined with a RIS (Radiology Information System). According to such a radiation image capturing system, in order to acquire desired radiation image information of a patient, a doctor sets patient information, including the name, gender, age, etc., of the patient, and image capturing conditions, including an image capturing apparatus to be used, the number of radiation images to be captured, and exposure conditions for determining a dosage level of radiation to be applied to a body region to be imaged. The doctor then supplies such information items as an image capturing order to a console, which is installed in a radiological department. The radiological technician who handles the image capturing apparatus operates the console, and controls the image capturing apparatus according to the supplied image capturing order, in order to acquire radiation image information of the patient. After the acquired radiation image information has been processed, the radiation image information is supplied to a viewer, which displays radiation images to be interpreted by the doctor for diagnosis.

For capturing a radiation image of the patient, the radiological technician positions a region of the body to be imaged with respect to the image capturing apparatus, according to the image capturing conditions set by the image capturing order, and then turns on an exposure switch of the image capturing apparatus in order to capture the radiation image. Radiation image information representing the captured radiation image is displayed on the console.

The image capturing order, which is prepared by the doctor, may not necessarily be capable of performing an appropriate image capturing process at all times. For example, if the image capturing apparatus specified by the doctor is already in use, or cannot be used due to a failure, then the radiological technician is required to change to another image capturing apparatus, having functions equivalent to those of the specified image capturing apparatus, in order to capture the desired radiation images. A certain body region to be imaged may be too large, and thus has to be divided into a plurality of segments that must be imaged separately. In such a case, the number of radiation images set in the image capturing order differs from the actual number of radiation images to be captured. Furthermore, if the image capturing order prepared by the doctor contains an obvious mistake therein, then the image capturing order has to be corrected. Moreover, depending on the settings of the image capturing apparatus, or for the convenience of the radiological technician, the image capturing process may be made more efficient if the supplied image capturing order is changed to a different order or sequence of radiation images.

As described above, at the site where radiation image information actually is captured, the radiation images may not necessarily be captured according to the image capturing order from the doctor. However, if the radiological technician prepares a report on the captured radiation images that deviates from the supplied image capturing process, then the doctor could possibly judge that the report resulted from an inappropriate image capturing process. Normally, if the radiological technician wants to alter the image capturing order received from the doctor, the radiological technician must first make a request to the doctor in advance in order to correct the image capturing order, or prepare a report on the captured radiation images together with comments, which indicate that the image capturing order has been changed, after the image capturing process is performed.

According to the system disclosed in Japanese Laid-Open Patent Publication No. 2000-166908, if a radiological technician changes the sequence of radiation images indicated by the image capturing order from the doctor, and captures radiation images according to a different changed sequence, then after the image capturing process is performed, the system sorts the captured radiation images into the sequence indicated by the image capturing order from the doctor, and subsequently prepares a report on the captured radiation images. However, the report prepared in the disclosed system does not reflect the actual image capturing details, such as a changed image capturing apparatus, a changed number of captured radiation images, etc.

SUMMARY OF THE INVENTION

It is an object of the present invention to, when an image capturing order is changed, enable acquired radiation image information to be recognized appropriately by supplying image capturing details for the changed image capturing order.

A radiation image capturing system according to the present invention includes an image capturing apparatus for acquiring radiation image information of a subject by controlling a radiation source according to predetermined image capturing conditions, an image capturing order supply apparatus for supplying an image capturing order including the image capturing conditions, and a controller for controlling the image capturing apparatus according to the image capturing order. The controller includes an image capturing order changer for changing the image capturing order, an image capturing detail editor for editing image capturing details of the radiation image information acquired when the image capturing apparatus is controlled according to the image capturing order, and an image capturing detail supply unit for supplying the edited image capturing details.

Further, a controller according to the present invention also is provided, wherein, in the case that an image capturing apparatus for acquiring radiation image information of a subject by controlling a radiation source according to predetermined image capturing conditions, and an image capturing order supply apparatus for supplying an image capturing order including the image capturing conditions, are provided, the controller controls the image capturing apparatus according to the image capturing order supplied from the image capturing order supply apparatus. The controller comprises an image capturing order changer for changing the image capturing order, an image capturing detail editor for editing image capturing details of the radiation image information acquired when the image capturing apparatus is controlled according to the image capturing order, and an image capturing detail supply unit for supplying the edited image capturing details.

Furthermore, a program executed in a controller also is provided, wherein, in the case that an image capturing apparatus for acquiring radiation image information of a subject by controlling a radiation source according to predetermined image capturing conditions, and an image capturing order supply apparatus for supplying an image capturing order including the image capturing conditions, are provided, the program controls the image capturing apparatus according to the image capturing order supplied from the image capturing order supply apparatus. The program comprises a step of changing the image capturing order, performed by an image capturing order changer of the controller, a step of editing image capturing details of the radiation image information acquired when the image capturing apparatus is controlled according to the image capturing order, performed by an image capturing detail editor of the controller, and a step of supplying the edited image capturing details, performed by an image capturing detail supply unit of the controller.

Still further, a radiation image capturing method is provided, wherein, in the case that an image capturing apparatus for acquiring radiation image information of a subject by controlling a radiation source according to predetermined image capturing conditions, an image capturing order supply apparatus for supplying an image capturing order including the image capturing conditions, and a controller that controls the image capturing apparatus according to the image capturing order are provided, the method comprises the steps of changing the image capturing order, performed by an image capturing order changer of the controller, editing image capturing details of the radiation image information acquired when the image capturing apparatus is controlled according to the image capturing order, performed by an image capturing detail editor of the controller, and supplying the edited image capturing details, performed by an image capturing detail supply unit of the controller.

According to these inventions, when the image capturing order is changed, the image capturing details of the radiation image information acquired based on the changed image capturing order are edited and supplied. Therefore, the acquired radiation image information can appropriately be grasped according to the image capturing details.

The above and other objects, features, and advantages of the present invention will become more apparent from the following description when taken in conjunction with the accompanying drawings in which a preferred embodiment of the present invention is shown by way of illustrative example.

DESCRIPTION OF THE PREFERRED EMBODIMENT

Figure 1:
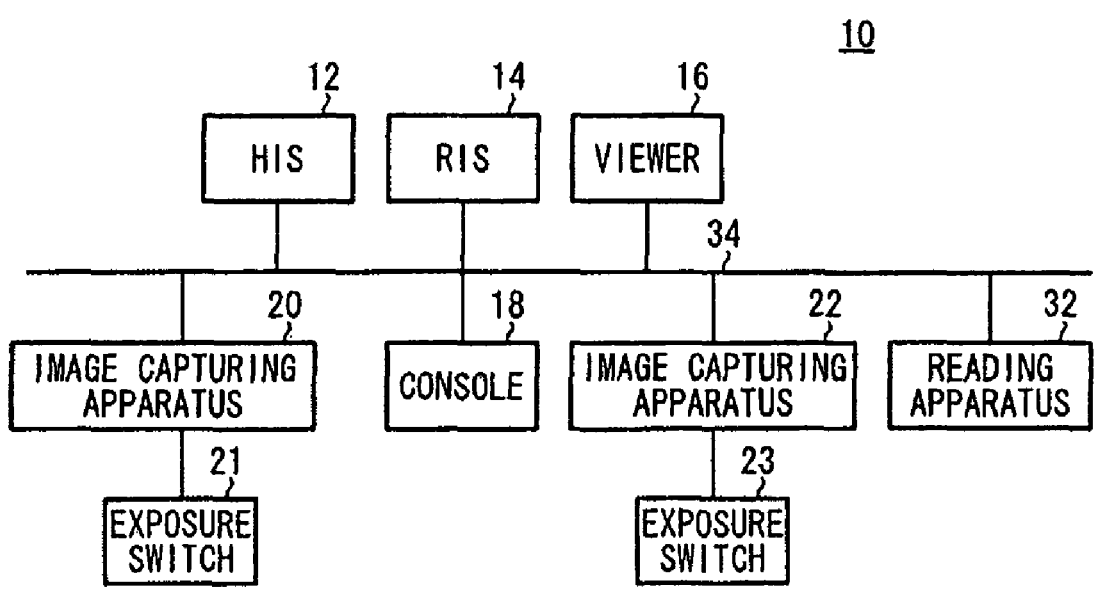
FIG. 1 is a block diagram of a radiation image capturing system according to an embodiment of the present invention.
Figure 2:
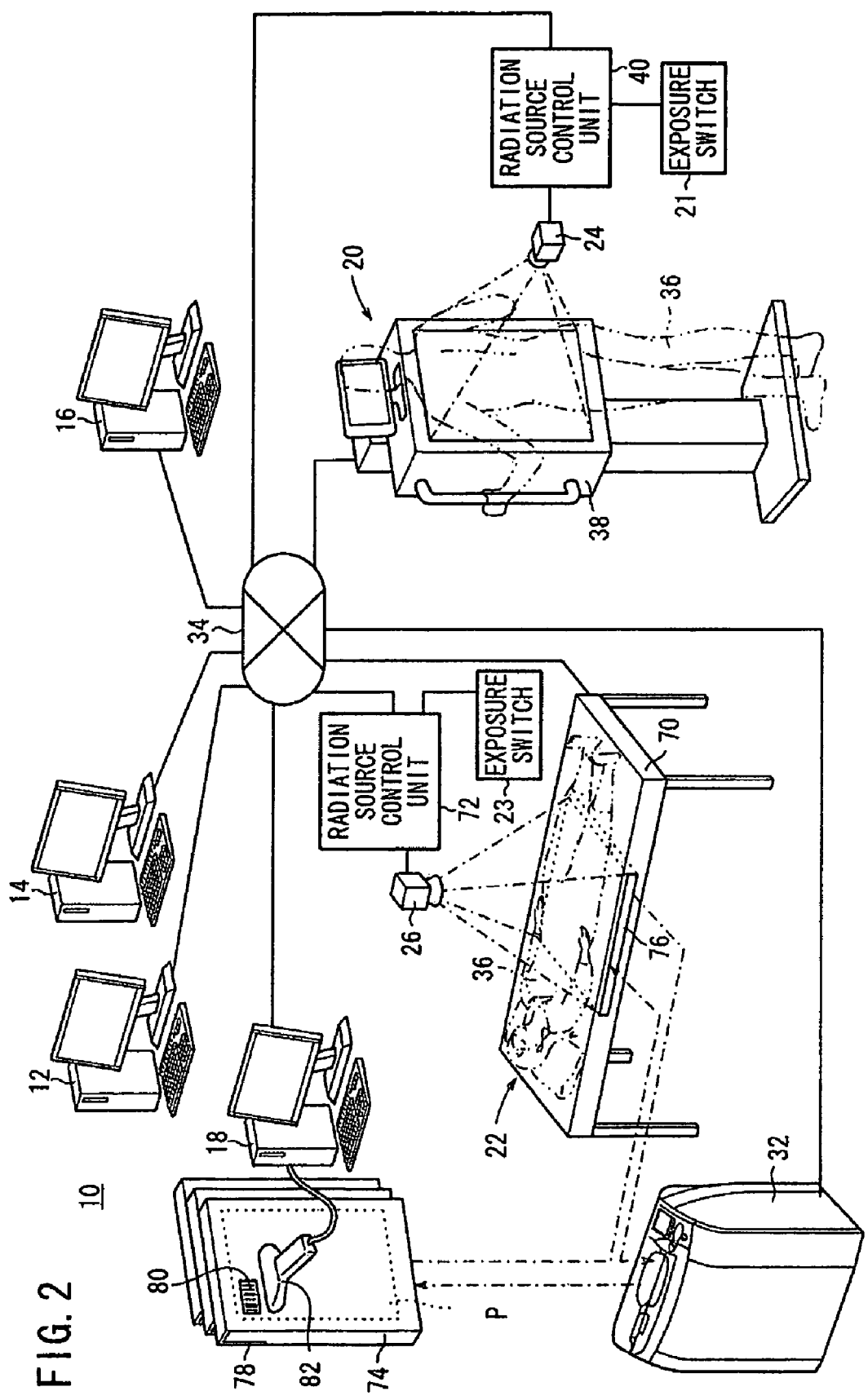
FIG. 2 is a schematic perspective view of the radiation image capturing system shown in FIG. 1.

FIGS. 1 and 2 show a configuration of a radiation image capturing system 10 according to an embodiment of the present invention. As shown in FIGS. 1 and 2, the radiation image capturing system 10 comprises a hospital information system (HIS) 12 for managing medical information in a hospital, a radiology information system (RIS) (image capturing order supply apparatus) 14 for managing radiation image capturing processes performed in the radiological department of the hospital under the management of the HIS 12, a viewer 16 for displaying radiation images to be interpreted by the doctor for diagnosis, a console (controller) 18 placed in a control room near image capturing rooms in the radiological department for managing various image capturing apparatus having different specifications through execution of a program stored in a non-illustrated memory, a pair of respective image capturing apparatus 20, 22 placed in the image capturing rooms, a pair of exposure switches 21, 23 for energizing respective radiation sources 24, 26 of the image capturing apparatus 20, 22 for applying radiation to subjects, and a reading apparatus 32 for reading radiation image information recorded in a radiation conversion panel P by the image capturing apparatus 22. The above components of the radiation image capturing system 10 are interconnected by an in-house network 34 in the hospital. If necessary, other consoles, image capturing apparatus, and components may also be connected to the in-house network 34.

The image capturing apparatus 20 comprises an image capturing base 38 for acquiring radiation image information of a subject 36 in an upstanding posture, a radiation source 24, and a radiation source control unit 40 for controlling the radiation source 24 according to an exposure signal from the exposure switch 21. The image capturing apparatus 20 incorporates therein a radiation conversion panel D (see FIG. 3) comprising a solid-state radiation detector for converting radiation into electric signals.

Figure 3:
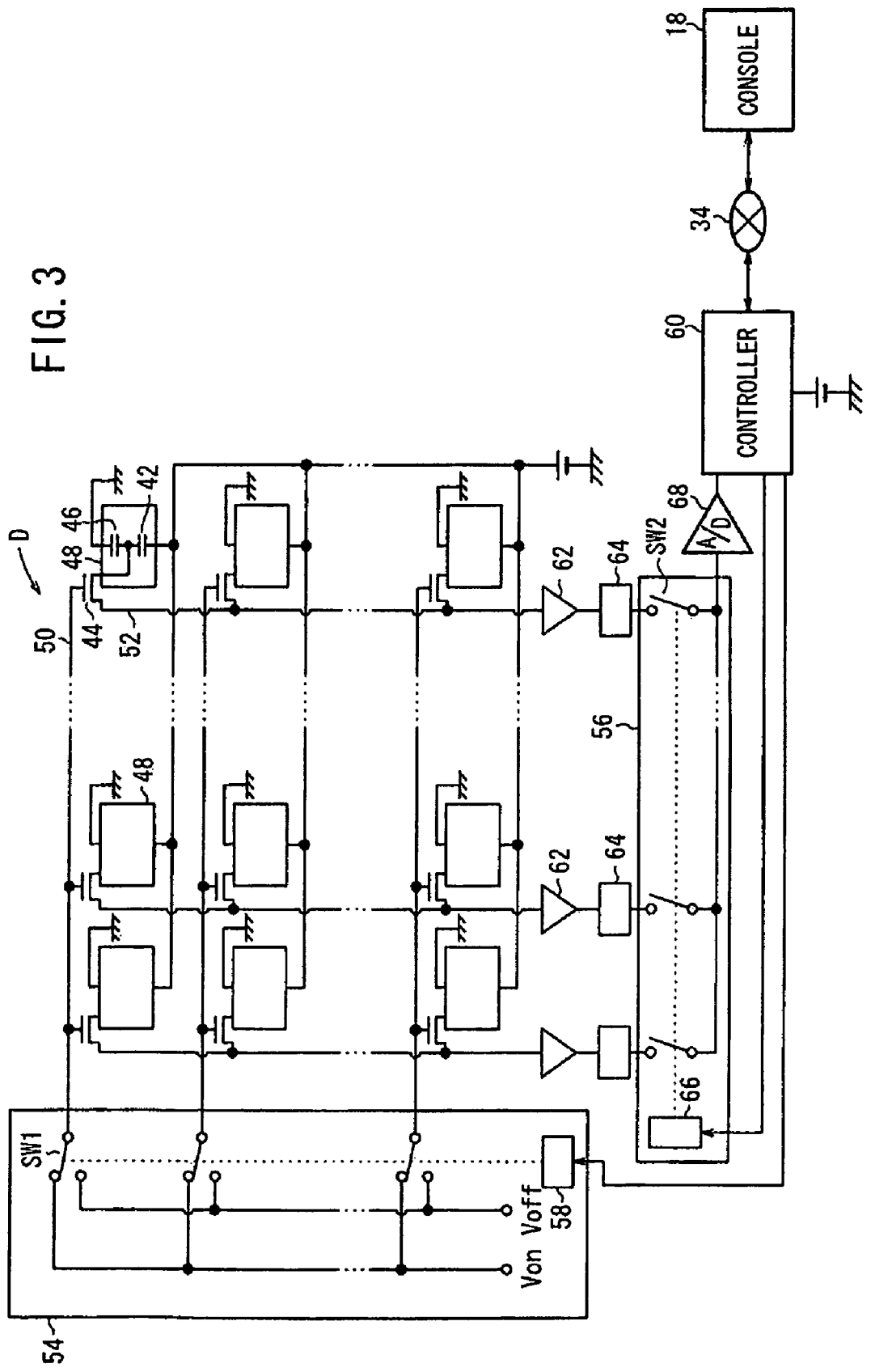
FIG. 3 is a block diagram of a circuit arrangement of a radiation conversion panel used in an image capturing apparatus shown in FIG. 1.

FIG. 3 shows in block form a circuit arrangement of the radiation conversion panel D housed in the image capturing base 38.

The radiation conversion panel D comprises an array of thin-film transistors (TFTs) 44 arranged in rows and columns, a photoelectric conversion layer 42 made of a material such as amorphous selenium (a-Se) for generating electric charges upon detection of radiation, the photoelectric conversion layer 42 being disposed on the array of TFTs 44, and an array of storage capacitors 46 connected to the photoelectric conversion layer 42. When radiation is applied to the radiation conversion panel D, the photoelectric conversion layer 42 generates electric charges, and the storage capacitors 46 store the generated electric charges. Then, the TFTs 44 are turned on, one row at a time, in order to read the electric charges from the storage capacitors 46 as an image signal. In FIG. 3, the photoelectric conversion layer 42 and one of the storage capacitors 46 are shown as forming one pixel 48 (image element), with the pixel 48 being connected to one of the TFTs 44. Details of other pixels 48 have been omitted from illustration for the sake of simplicity. Since amorphous selenium tends to change its structure and lose functionality at high temperatures, amorphous selenium needs to be used within a certain temperature range. Therefore, some means for cooling the radiation conversion panel D should preferably be provided in the image capturing base 38.

The TFTs 44 connected to the respective pixels 48 are connected to respective gate lines 50 extending parallel to the rows, and to respective signal lines 52 extending parallel to the columns. The gate lines 50 are connected to a line scanning driver 54, and the signal lines 52 are connected to a multiplexer 56 that serves as a reading circuit.

The gate lines 50 are supplied with control signals Von, Voff from the line scanning driver 54 for turning on and off the TFTs 44 along the rows. The line scanning driver 54 comprises a plurality of switches SW1 for switching between the gate lines 50, and an address decoder 58 for outputting a selection signal for selecting one of the switches SW1 at a time. The address decoder 58 is supplied with an address signal from a controller 60.

The signal lines 52 are supplied with electric charges stored in the storage capacitors 46 of the pixels 48 through the TFTs 44 arranged in the columns. The electric charges supplied to the signal lines 52 are amplified by amplifiers 62 connected respectively to the signal lines 52. The amplifiers 62 are connected through respective sample and hold circuits 64 to the multiplexer 56. The multiplexer 56 comprises a plurality of switches SW2 for successively switching between the signal lines 52, and an address decoder 66 for outputting a selection signal for selecting one of the switches SW2 at a time. The address decoder 66 is supplied with an address signal from the controller 60. The multiplexer 56 has an output terminal connected to an A/D converter 68. A radiation image signal generated by the multiplexer 56 based on the electric charges from the sample and hold circuits 64 is converted by the A/D converter 68 into a digital image signal representing radiation image information, which is supplied to the controller 60. The controller 60 supplies the acquired radiation image information through the in-house network 34 to the console 18.

The TFTs 44, which function as switching elements, may be realized in combination with a CMOS (complementary metal-oxide semiconductor) image sensor or the like, or with other types of imaging devices. Still further, the TFTs 44 may be replaced by CCD (charge-coupled device) sensors, which transmit charges while shifting the charges by means of shift pulses, corresponding to the gate signals within the TFTs.

The image capturing apparatus 22 comprises an image capturing base 70 for acquiring radiation image information of a subject 36 lying in a recumbent posture, a radiation source 26, and a radiation source control unit 72 for controlling the radiation source 26 according to an exposure signal from the exposure switch 23. The image capturing base 70 has a slot 76, defined in a side wall thereof, through which a cassette 74 housing a radiation conversion panel P in the form of a stimulable phosphor panel can be loaded into the image capturing base 70.

The radiation conversion panel P comprises a support body and a stimulable phosphor layer disposed on the support body. The stimulable phosphor layer stores energy of the radiation that is applied thereto. When the stimulable phosphor layer is irradiated with stimulating light, the stimulable phosphor layer emits stimulated light depending on the stored energy. When the stimulable phosphor layer is irradiated with erasing light, any remaining energy stored therein is discharged and the radiation conversion panel P can be reused.

The radiation conversion panel P housed in the cassette 74 is removable from the cassette 74 when a lid 78 on the cassette 74 is opened. A bar code 80, which has recorded therein identification information including a unique number for identifying the radiation conversion panel P housed in the cassette 74, the size of the radiation conversion panel P, the sensitivity of the radiation conversion panel P, etc., is applied to an outer surface of the cassette 74. The bar code 80 can be read by the bar-code reader 82, which is connected to the console 18.

The reading apparatus 32 serves to read the radiation image information recorded in the radiation conversion panel P. The reading apparatus 32 is constructed as shown in FIG. 4.

Figure 4:
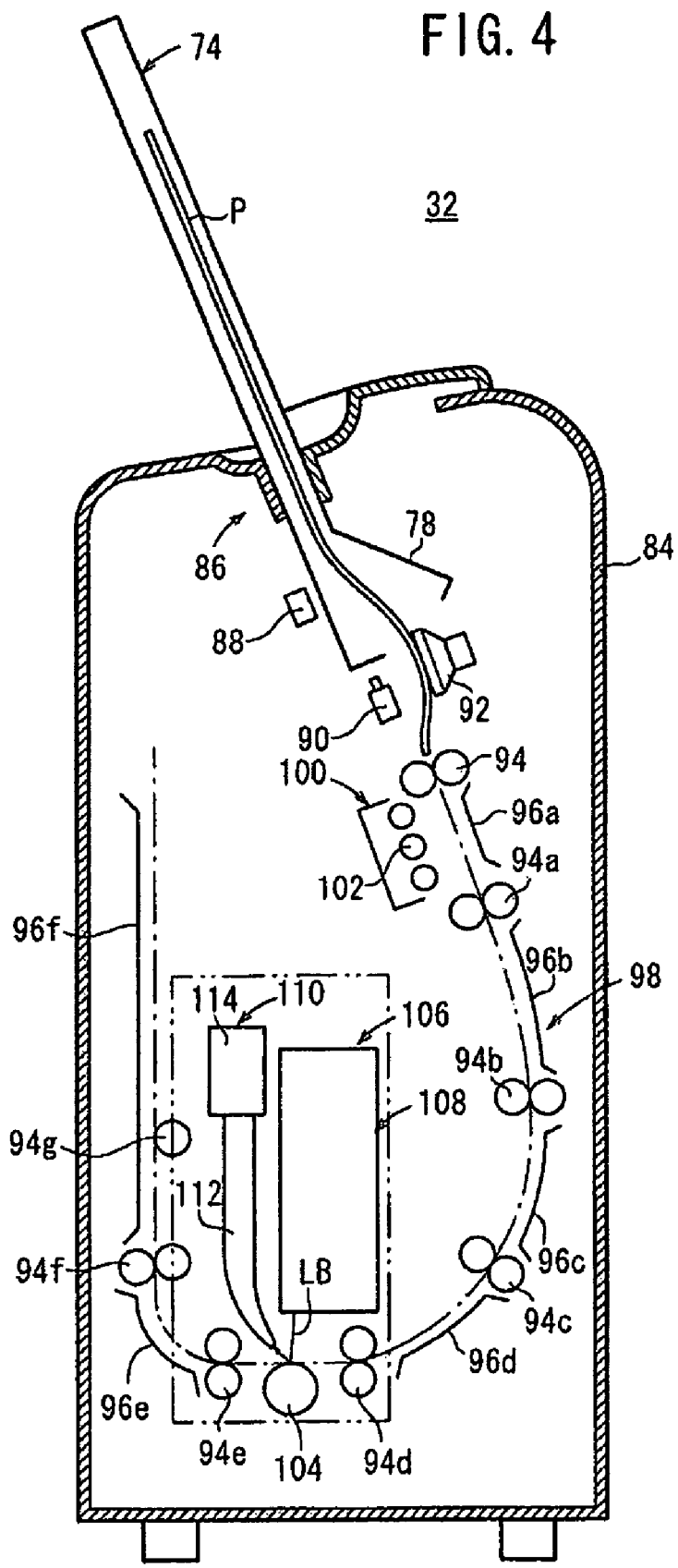
FIG. 4 is a vertical cross-sectional view of a reading apparatus of the radiation image capturing system.

As shown in FIG. 4, the reading apparatus 32 has a cassette loader 86 disposed in an upper portion of a casing 84. The cassette 74, which houses therein the radiation conversion panel P with recorded radiation image information, is loaded into the cassette loader 86. The casing 84 of the reading apparatus 32 accommodates therein, near the cassette loader 86, a bar-code reader 88 for reading the identification information recorded in the bar code 80 on the cassette 74, an unlocking mechanism 90 for unlocking the lid 78 of the cassette 74, a suction cup 92 for attracting and removing the radiation conversion panel P from the cassette 74 at the time the lid 78 is opened, and a pair of nip rollers 94 for gripping and feeding the radiation conversion panel P removed by the suction cup 92.

The nip rollers 94 are followed by a plurality of feed rollers 94a through 94g and a plurality of guide plates 96a through 96f, which jointly make up a curved feed path 98. The curved feed path 98 extends downwardly from the cassette loader 86, then extends substantially horizontally at its lowermost portion, and then extends substantially vertically upward. The shape of the curved feed path 98 is effective to make the reading apparatus 32 small in size.

Between the nip rollers 94 and the feed rollers 94a, an erasing unit 100 is disposed for erasing the radiation image information remaining in the radiation conversion panel P, from which desired radiation image information has been read. The erasing unit 100 has a plurality of erasing light sources 102, such as cold cathode-ray tubes or the like, for emitting erasing light.

A platen roller 104 is disposed between the feed rollers 94d, 94e, which are positioned in the lowermost portion of the curved feed path 98. The platen roller 104 is disposed beneath a scanning unit 106 for reading the desired radiation image information recorded in the radiation conversion panel P.

The scanning unit 106 comprises a stimulator 108 for emitting a laser beam LB as stimulating light to scan the radiation conversion panel P, and a reader 110 for reading stimulated light emitted from the radiation conversion panel P, which is stimulated by the laser beam LB.

The reader 110 comprises a light guide 112 having a lower end disposed near the radiation conversion panel P over the platen roller 104, and a photomultiplier 114 connected to an upper end of the light guide 112 for converting the stimulated light from the radiation conversion panel P into electric signals representing the radiation image information stored in the radiation conversion panel P. The photomultiplier 114 supplies the electric signals representing the radiation image information to the console 18 through the in-house network 34.

Figure 5:
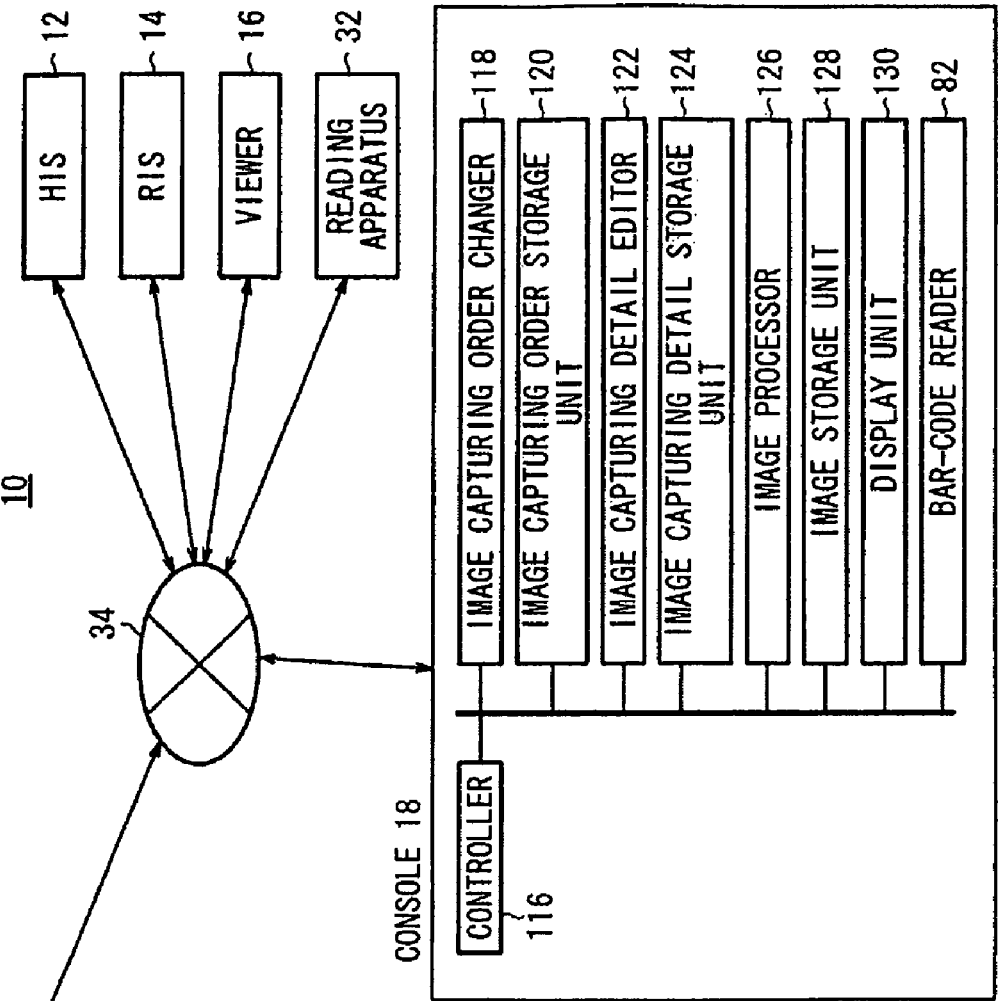
FIG. 5 is a block diagram of a console, an image capturing apparatus, and other components of the radiation image capturing system shown in FIG. 1.

FIG. 5 shows in block form the console 18, the image capturing apparatus 20, 22, and other components of the radiation image capturing system 10 shown in FIG. 1.

As shown in FIG. 5, the console 18 includes a controller (image capturing detail supply unit) 116 for controlling the console 18 in its entirety. Through execution of the aforementioned program, the controller 116 acquires, through the in-house network 34, an image capturing order. The image capturing order comprises patient information, including the name, gender, age, etc., of the patient, which has been set using the HIS 12, and image capturing conditions including an image capturing method for capturing radiation image information of the patient, a body region to be imaged, an image capturing apparatus to be used, the number of radiation images to be captured, and exposure conditions including a tube voltage, a tube current, a radiation exposure time, etc., to be set in the radiation source of the image capturing apparatus, which have been set by the doctor using the RIS 14.

To the controller 116, there are connected an image capturing order changer 118 for changing an image capturing order, an image capturing order storage unit 120 for storing an unchanged image capturing order supplied from the in-house network 34 and a changed image capturing order, an image capturing detail editor 122 for editing image capturing details of the radiation image information captured by the image capturing apparatus 20, 22, an image capturing detail storage unit 124 for storing edited image capturing details, an image processor 126 for processing radiation image information, an image storage unit 128 for storing unprocessed radiation image information and processed radiation image information, a display unit 130 for displaying an image capturing order and radiation image information, and a bar-code reader 82 for reading the bar code 80 on the cassette 74.

Figure 6:
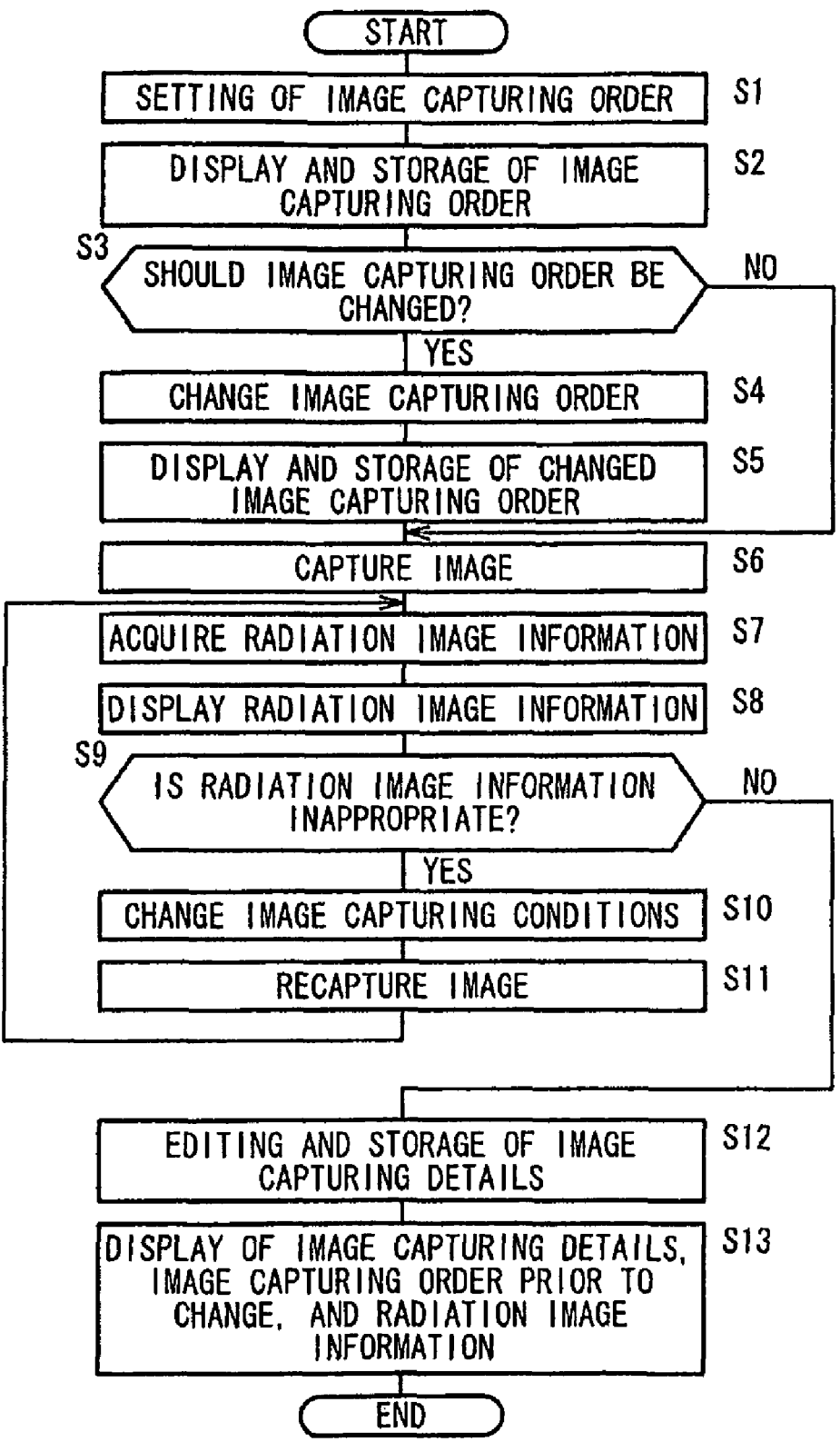
FIG. 6 is a flowchart for explaining operations of the system shown in FIG. 1.

The radiation image capturing system 10 according to the present invention is basically constructed as described above. Next, operations (a radiation image capturing method) of the radiation image capturing system 10 shall be described below with reference to the flowchart of FIG. 6.

First, patient information such as the name, gender, age, etc., of a patient is set using the HIS 12. Then, using the RIS 14, the doctor sets image capturing conditions in relation to the patient information, including an image capturing method for capturing radiation image information of the patient, a body region to be imaged, an image capturing apparatus to be used, the number of radiation images to be captured, and exposure conditions including a tube voltage, a tube current, a radiation exposure time, etc., to be set in the radiation source of the image capturing apparatus (step S1). The patient information and the image capturing conditions set using the HIS 12 and the RIS 14 are sent as an image capturing order via the in-house network 34 to the console 18, which is installed in the radiological department. The image capturing order is stored in the image capturing order storage unit 120 unit of the console 18. A program stored in a non-illustrated memory is executed in the console 18. The controller 116 of the console 18 displays the sent image capturing order on the display unit 130 (step S2). A plurality of image capturing orders may be set for a plurality of patients.

The radiological technician in the radiological department then confirms the image capturing order displayed on the display unit 130 (step S3). In this case, if the image capturing apparatus specified by the image capturing order is currently in use, being serviced for maintenance, or is suffering a failure (YES in step S3), then the radiological technician changes the image capturing apparatus to another image capturing apparatus, which can be used, using the image capturing order changer 118 (step S4). Further, if the number of radiation images to be captured, which has been set by the doctor, needs to be changed due to the size of the body region to be imaged, or if the settings made by the doctor are in error (YES in step S3), then the radiological technician changes the number of radiation images to be captured using the image capturing order changer 118 (step S4). The radiological technician may similarly change the image capturing order, including the exposure conditions depending on the age, gender, body conditions, etc., of the subject 36, using the image capturing order changer 118 (step S4). The changed image capturing order, as well as the unchanged image capturing order produced by the doctor, are stored in the image capturing order storage unit 120. Further, the changed image capturing order is displayed on the display unit 130 (step S5).

After the radiological technician has confirmed the image capturing order, or changed the image capturing order if necessary, the radiological technician initiates capturing of the radiation image information of the subject 36 according to the image capturing order (step S6). The radiological technician selects the image capturing order for the subject 36 to be imaged, among image capturing orders which are being displayed on the display unit 130. Then, the radiological technician guides the subject 36 to the image capturing apparatus, as set in the selected image capturing order.

If the image capturing apparatus 20 is set in the selected image capturing order, then the radiological technician guides the subject 36 to the image capturing apparatus 20. The radiological technician adjusts the position of the image capturing base 38, adjusts the imaging posture of the subject 36, and makes other necessary adjustments. The controller 116 of the console 18 sends the exposure conditions set in the selected image capturing order to the radiation source control unit 40 of the image capturing apparatus 20. At this time, the exposure conditions, including the tube voltage, the tube current, the radiation exposure time, etc., for the radiation source 24, are set in the radiation source control unit 40.

When the radiological technician presses the exposure switch 21, an exposure signal is sent through the radiation source control unit 40 to the radiation source 24. In response to the exposure signal, the radiation source 24 outputs radiation, which is controlled according to the exposure conditions that are set in the radiation source control unit 40, and radiation is applied to the subject 36.

Radiation that has passed through the subject 36 is applied to the radiation conversion panel D housed in the image capturing base 38, thereby recording radiation image information of the subject 36 in the radiation conversion panel D.

The radiation is converted into electric signals by the photoelectric conversion layer 42 of the pixels 48 of the radiation conversion panel D (FIG. 3). The electric signals are stored as electric charges in the storage capacitors 46. The stored electric charges, which represent radiation image information of the subject 36, are read from the storage capacitors 46 according to address signals, which are supplied from the controller 60 to the line scanning driver 54 and the multiplexer 56.

Specifically, in response to the address signal supplied from the controller 60, the address decoder 58 of the line scanning driver 54 outputs a selection signal to select one of the switches SW1, which supplies the control signal Von to the gates of the TFTs 44 connected to the gate line 50 corresponding to the selected switch SW1. In response to the address signal supplied from the controller 60, the address decoder 66 of the multiplexer 56 outputs a selection signal that successively turns the switches SW2 on in order to switch between the signal lines 52, for thereby reading via the signal lines 52 the electric charges stored in the storage capacitors 46 of the pixels 48 connected to the selected gate line 50.

The electric charges read from the storage capacitors 46 of the pixels 48 connected to the selected gate line 50 are amplified by the respective amplifiers 62, sampled by the sample and hold circuits 64, and supplied to the multiplexer 56. Based on the supplied electric charges, the multiplexer 56 generates and supplies a radiation image signal to the A/D converter 68, which converts the radiation image signal into a digital signal. The digital signal, which represents the radiation image information, is transmitted from the controller 60 to the console 18 through the in-house network 34 (step S7).

Similarly, the address decoder 58 of the line scanning driver 54 successively turns on the switches SW1 to switch between the gate lines 50, according to the address signal supplied from the controller 60. The electric charges stored in the storage capacitors 46 of the pixels 48 connected to the successively selected gate lines 50 are read through the signal lines 52, and processed by the multiplexer 56 and the A/D converter 68 into digital signals, which are transmitted from the controller 60 to the console 18 through the in-house network 34 (step S7).

The image processor 126 of the console 18 processes the received radiation image information, stores the processed radiation image information in the image storage unit 128, and displays the processed radiation image information on the display unit 130 (step S8).

The radiological technician confirms the radiation image information of the subject 36 that is displayed on the display unit 130 (step S9). If the radiological technician judges that the displayed radiation image information is inappropriate (YES in step S9), then the technician changes some of the image capturing conditions with the image capturing order changer 118 (step S10), readjusts the image capturing posture of the subject 36 and the body region to be imaged of the subject 36, sets the changed image capturing conditions in the radiation source control unit 40, and captures radiation image information of the subject 36 again (step S11). The changed image capturing conditions are stored in the image capturing order storage unit 120.

When desired radiation image information has been acquired (NO in step S9), the image capturing detail editor 122 edits the patient information and the image capturing conditions, including the body region to be captured, the image capturing apparatus, the number of radiation images to be captured, and the exposure conditions, with respect to the radiation image information, and stores the edited details in the image capturing detail storage unit 124 (step S12). If the number of captured radiation images is smaller than the number of radiation images to be captured set in the image capturing order prepared by the doctor, then further image capturing details may be recorded, which include an mAs value (the product of the tube current and the exposure time) of 0, representing the radiation dosage level, as an exposure condition for uncaptured radiation images in the image capturing order.

Next, the image capturing details stored in the image capturing detail storage unit 124 are sent, together with the unchanged image capturing order stored in the image capturing order storage unit 120, and the radiation image information stored in the image storage unit 128, to the viewer 16 through the in-house network 34 (step S13). The doctor then diagnostically interprets the radiation image that is displayed by the viewer 16 based on the radiation image information.

Since the doctor can compare the image capturing order prepared thereby and the image capturing details based on the image capturing order changed by the radiological technician, the doctor can confirm and verify the radiation image information acquired according to the changed image capturing order, based on the image capturing details, while taking into account the circumstances under which the radiation image information was captured.

An image capturing process in which an image capturing apparatus 22 is set in the image capturing order will be described below.

The radiological technician guides the subject 36 to the image capturing apparatus 2, and adjusts the image capturing position of the subject 36 with respect to the image capturing base 70. The controller 116 of the console 18 sends the exposure conditions set in the selected image capturing order to the radiation source control unit 72 of the image capturing apparatus 22. The exposure conditions, including a tube voltage, a tube current, a radiation exposure time, etc., for the radiation source 26, are set in the radiation source control unit 72.

The radiological technician uses the bar-code reader 82 connected to the console 18 to read the bar code 80 applied to the cassette 74, thereby acquiring identification information, including a unique number for identifying the radiation conversion panel P housed in the cassette 74, the size of the radiation conversion panel P, the sensitivity of the radiation conversion panel P, etc.

After the cassette 74 has been loaded into the slot 76 of the image capturing apparatus 22, the radiological technician presses the exposure switch 23. The radiation source 26 outputs and applies radiation to the subject 36.

Radiation that has passed through the subject 36 is applied to the radiation conversion panel P housed in the cassette 74. As a result, radiation image information of the subject 36 is recorded in the radiation conversion panel P.

The radiological technician then removes the cassette 74, which houses therein the radiation conversion panel P with the recorded radiation image information from the image capturing apparatus 22, and thereafter loads the cassette 74 into the cassette loader 86 of the reading apparatus 32.

When the cassette 74 is loaded into the cassette loader 86, the bar-code reader 88 in the cassette loader 86 reads the bar code 80 applied to the cassette 74 in order to acquire the identification information, including the unique number, the size, the sensitivity, etc., of the radiation conversion panel P. The acquired identification information is compared with the identification information read by the bar-code reader 82 connected to the console 18, in order to confirm the correspondence between the subject 36 and the radiation image information.

After the identification information has been read, the unlocking mechanism 90 is actuated to unlock and open the lid 78. The suction cup 92 attracts the radiation conversion panel P, removes the radiation conversion panel P from the cassette 74, and feeds the radiation conversion panel P between the nip rollers 94. The radiation conversion panel P, which is gripped by the nip rollers 94, is then fed through the curved feed path 98, made up of the feed rollers 94a through 94g and the guide plates 96a through 96f, to a position beneath the scanning unit 106.

Beneath the scanning unit 106, the panel P is fed substantially horizontally in an auxiliary scanning direction by the feed rollers 94d, 94e. At the same time, a laser beam LB output from the stimulator 108 is guided to the radiation conversion panel P, thereby scanning the radiation conversion panel P in a main scanning direction, which is perpendicular to the auxiliary scanning direction.

As a result of being irradiated with the laser beam LB, the radiation conversion panel P is stimulated to emit stimulated light representative of the radiation image information recorded therein. The stimulated light is applied to the lower end of the light guide 112, which is disposed near the radiation conversion panel P and extends in the main scanning direction. The stimulated light, which has entered the light guide 112, is repeatedly reflected in the light guide 112 and guided to the photomultiplier 114. The photomultiplier 114 converts the stimulated light into electric signals representative of the radiation image information recorded in the radiation conversion panel P. In this manner, the radiation image information recorded in the radiation conversion panel P is read by the scanning unit 106 of the reading apparatus 32 (step S7).

The radiation image information thus read by the scanning unit 106 is transmitted to the console 18 through the in-house network 34. The controller 116 of the console 18 displays a radiation image based on the radiation image information (step S8), and the radiological technician confirms the radiation image (step S9). If necessary, the radiological technician changes the image capturing order and recaptures radiation image information of the subject 36 again (steps S10, S11). The changed image capturing order is stored in the image capturing order storage unit 120.

Once desired radiation image information has been acquired (NO in step S9), the image capturing detail editor 122 edits the patient information and the image capturing conditions with respect to the radiation image information, and stores the edited details in the image capturing detail storage unit 124 (step S12).

The image capturing details stored in the image capturing detail storage unit 124 are sent, together with the unchanged image capturing order stored in the image capturing order storage unit 120 and the radiation image information stored in the image storage unit 128, to the viewer 16 through the in-house network 34 (step S13). The doctor then diagnostically interprets the radiation image that is displayed by the viewer 16 based on the radiation image information.

Although a certain preferred embodiment of the present invention has been shown and described in detail, it should be understood that various changes and modifications may be made to the embodiment without departing from the scope of the invention has set forth in the appended claims.

For example, the aforementioned radiation conversion panel D makes up a direct-conversion type of radiation detector, which converts the radiation dose of the irradiated radiation directly into electric signals through the photoelectric conversion layer 42. However, in place of this structure, a indirect-conversion type of radiation detector in which irradiated radiation is converted initially into visible light by a scintillator, and thereafter, the visible light is converted into electric signals using a solid-state detecting device formed from amorphous silicon (a-Si) or the like, may also be used (see, Japanese Patent No. 3494683).

Further, the radiation image information can be obtained using a light readout type of radiation detector. With such a light readout type of radiation detector, radiation is irradiated onto respective solid state detecting devices arranged in a matrix form, and an electrostatic latent image corresponding to the irradiation dose is stored cumulatively in the solid state detecting devices. When the electrostatic latent image is read, reading light is irradiated onto the radiation detector, and the generated current values are acquired as radiation image information. Further, by irradiating the radiation detector with erasing light, the radiation image information in the form of a residual electrostatic latent image can be erased and the radiation detector can be reused (see, Japanese Laid-Open Patent Publication No. 2000-105297).

Furthermore, in the present embodiment, a case has been described in which patient information is set in the HIS 12 by a doctor, image capturing instruction information is set in the RIS 14 by a doctor or a technician, and such information is supplied to the console 18 over the hospital network 34. However, in place of this configuration, the patient information and image capturing instruction information may also be set directly in the console 18, or alternatively, the patient information and image capturing instruction information may be set either by the HIS 12 or the RIS 14.

What is claimed is:

1. A radiation image capturing system comprising:
    an image capturing apparatus for acquiring radiation image information of a subject by controlling a radiation source according to predetermined image capturing conditions;
    an image capturing order supply apparatus for supplying an image capturing order including the image capturing conditions; and
    a controller for controlling the image capturing apparatus according to the image capturing order; and
    a viewer for interpretation of the radiation image by a doctor for diagnosis,
    wherein the controller comprises:
    an image capturing order changer for changing the image capturing order;
    an image capturing detail editor for editing image capturing details of the radiation image information acquired when the image capturing apparatus is controlled according to a changed image capturing order; and
    an image capturing detail supply unit for supplying the image capturing order prior to change, the edited image capturing details, and the radiation image information acquired by the image capturing apparatus according to the changed image capturing order, to the viewer.

2. A radiation image capturing system according to claim 1, further comprising a display unit for displaying the image capturing order supplied from the image capturing order supply apparatus and the image capturing details supplied from the image capturing detail supply unit.

3. A radiation image capturing system according to claim 1, wherein the image capturing order represents information as to the number of radiation images that make up the radiation image information.

4. A radiation image capturing system according to claim 1, wherein the image capturing order represents information as to the image capturing apparatus.

5. The radiation image capturing system according to claim 1, where the image capturing order prior to change which is displayed at the viewer includes at least one of: a number of radiation images captured, radiation exposure amounts; radiation exposure time, and identification of imaging device acquiring the radiation image information.

6. The radiation image capturing system according to claim 5, wherein the changed image capturing order updates at least one of: a number of radiation images captured, radiation exposure amounts; radiation exposure time, and identification of imaging device acquiring the radiation image information, wherein the radiation image information acquired is according to the changed image capturing order.

7. A controller wherein, in the case that an image capturing apparatus for acquiring radiation image information of a subject by controlling a radiation source according to predetermined image capturing conditions, an image capturing order supply apparatus for supplying an image capturing order including the image capturing conditions, and a viewer for interpretation of radiation image by a doctor for diagnosis, are provided, the controller controls the image capturing apparatus according to the image capturing order supplied from the image capturing order supply apparatus, the controller comprising:
    an image capturing order changer for changing the image capturing order;
    an image capturing detail editor for editing image capturing details of the radiation image information acquired when the image capturing apparatus is controlled according to a changed image capturing order; and an image capturing detail supply unit for supplying the image capturing order prior to change, the edited image capturing details, and the radiation image information acquired by the image capturing apparatus according to the changed image capturing order, to the viewer.

8. A program executed in a controller wherein, in the case that an image capturing apparatus for acquiring radiation image information of a subject by controlling a radiation source according to predetermined image capturing conditions, an image capturing order supply apparatus for supplying an image capturing order including the image capturing conditions, and a viewer for interpretation of the radiation image by a doctor for diagnosis, are provided, the program controls the image capturing apparatus according to the image capturing order supplied from the image capturing order supply apparatus, the program comprising:

a step of changing the image capturing order, performed by an image capturing order changer of the controller;

a step of editing image capturing details of the radiation image information acquired when the image capturing apparatus is controlled according to a changed image capturing order, performed by an image capturing detail editor of the controller; and a step of supplying the image capturing order prior to change, the edited image capturing details, and the radiation image information acquired by the image capturing apparatus according to the changed image capturing order, from an image capturing detail supply unit of the controller to the viewer.

9. A radiation image capturing method, in the case that an image capturing apparatus for acquiring radiation image information of a subject by controlling a radiation source according to predetermined image capturing conditions, an image capturing order supply apparatus for supplying an image capturing order including the image capturing conditions, a controller that controls the image capturing apparatus according to the image capturing order, and a viewer for interpretation of the radiation image by a doctor for diagnosis are provided, the method comprising the steps of:

changing the image capturing order, performed by an image capturing order changer of the controller;

editing image capturing details of the radiation image information acquired when the image capturing apparatus is controlled according to a changed image capturing order, performed by an image capturing detail editor of the controller; and supplying the image capturing order prior to change, the edited image capturing details, and the radiation image information acquired by the image capturing apparatus according to the changed image capturing order, from an image capturing detail supply unit of the controller to the viewer.

* * * * *